(12) United States Patent
Thogersen et al.

(10) Patent No.: US 8,257,318 B2
(45) Date of Patent: Sep. 4, 2012

(54) INJECTION DEVICE HAVING A ROTATABLE SCALE DRUM

(75) Inventors: Klaus Thogersen, Charlottenlund (DK); Thomas Dedenroth Miller, Bronshoj (DK); Martin von Bulov, Helsingor (DK); Peter Lundholm Jensen, Copenhagen (DK)

(73) Assignee: Novo Nordisk A/S, Bagsvaerd (DK)

( * ) Notice: Subject to any disclaimer, the term of this patent is extended or adjusted under 35 U.S.C. 154(b) by 266 days.

(21) Appl. No.: 11/815,137

(22) PCT Filed: Feb. 9, 2006

(86) PCT No.: PCT/EP2006/050800
§ 371 (c)(1),
(2), (4) Date: Nov. 13, 2008

(87) PCT Pub. No.: WO2006/084876
PCT Pub. Date: Aug. 17, 2006

(65) Prior Publication Data
US 2009/0254047 A1  Oct. 8, 2009

(30) Foreign Application Priority Data

Feb. 11, 2005  (EP) .................... 05002872
May 17, 2005  (DK) .................... 2005 00715
Sep. 8, 2005  (DK) .................... 2005 01252

(51) Int. Cl.
*A61M 5/00*  (2006.01)
(52) U.S. Cl. ........ 604/211; 604/207; 604/208; 604/263; 604/110; 604/192; 604/198

(58) Field of Classification Search .................. 604/110, 604/181, 187, 192–198, 263, 207, 208, 211
See application file for complete search history.

(56) References Cited

U.S. PATENT DOCUMENTS

| | | | |
|---|---|---|---|
| 4,865,591 A * | 9/1989 | Sams | ............................ 604/186 |
| 5,320,609 A | 6/1994 | Haber et al. | |
| 5,505,704 A | 4/1996 | Pawelka et al. | |

(Continued)

FOREIGN PATENT DOCUMENTS

DE  29703820  8/1998

(Continued)

OTHER PUBLICATIONS

European Search Report issued in connection with counterpart European Application No. 05002872.9, mailed Jul. 27, 2005.

(Continued)

*Primary Examiner* — Bhisma Mehta
*Assistant Examiner* — Edelmira Bosques
(74) *Attorney, Agent, or Firm* — Marc A. Began

(57) ABSTRACT

The application disclosed concerns an injection device for apportioning set doses of a drug from a reservoir (40) to a subject. The injection device comprises a rotatable scale drum (50) which is screwed out from the proximal end of the injection device when a does is set. The rotatable scale drum (50) is coupled to a piston rod drive (100, 130) through a push button (30) and a connector pipe (80). When setting a does, the push button (30) engages the scale drum (50) such that both the push button (30) and the scale drum (50) rotate away from the housing (10). During injection, the scale drum (50) is released from the push button (30) and engaged with the connector pipe (80) in order to rotate the piston rod (120).

10 Claims, 9 Drawing Sheets

U.S. PATENT DOCUMENTS

| | | | |
|---|---|---|---|
| 6,004,297 | A | 12/1999 | Steenfeldt-Jensen et al. |
| 6,048,336 | A | 4/2000 | Gabriel |
| 6,221,053 | B1 | 4/2001 | Walters et al. |
| 6,228,067 | B1 | 5/2001 | Gabriel |
| 7,291,132 | B2 | 11/2007 | DeRuntz et al. |
| 2002/0052578 | A1 | 5/2002 | Moller |
| 2002/0120235 | A1* | 8/2002 | Enggaard ............... 604/135 |
| 2004/0059299 | A1* | 3/2004 | Moller ............... 604/207 |
| 2005/0033244 | A1 | 2/2005 | Veasey et al. |

FOREIGN PATENT DOCUMENTS

| | | |
|---|---|---|
| DE | 29724186 | 5/2000 |
| DE | 10302163 | 7/2004 |
| EP | 0295075 B1 | 12/1988 |
| EP | 554995 | 8/1993 |
| EP | 0937471 A2 | 8/1999 |
| EP | 1000631 | 7/2002 |
| FR | 2684880 | 6/1993 |
| JP | H08-503874 A | 4/1996 |
| JP | 2002501790 A | 1/2002 |
| WO | WO9311813 | 6/1993 |
| WO | 9422507 A2 | 10/1994 |
| WO | WO9839041 | 9/1998 |
| WO | WO 99/38554 A1 | 8/1999 |
| WO | WO03075985 | 9/2003 |
| WO | WO2004002557 | 1/2004 |
| WO | 2004078239 A1 | 9/2004 |
| WO | WO 2004/078239 A1 | 9/2004 |
| WO | WO2004078241 | 9/2004 |

OTHER PUBLICATIONS

European Search Report issued in connection with counterpart European Application No. 05002998.2, mailed Aug. 18, 2005.

International Search Report and Written Opinion issued in connection with counterpart PCT Application No. PCT/EP2006/050800, mailed May 24, 2006.

International Preliminary Examination Report issued in connection with counterpart PCT Application No. PCT/EP2006/050800, mailed Aug. 23, 2007.

Office Action in U.S. Appl. No. 11/791,397, filed May 23, 2007 by Radmer et al,, Mailed May 13, 2009.

Din ISO Pen-Systems—Part 1: Glass Cylinders for Pen-Injectors for Medical Use (ISO 13926-1:2004), Text in German and English 2005 (Opposition EP1827538 Dated May 7, 2010; Haselmeier/Novo Nordisk).

ISO Pen-Injectors for Medical Use—Part 1: Pen-Injectors—Requirements and Test Methods 2000 $1^{st}$ Ed 12-15 (Opposition EP1827538 Dated May 7, 2010; Haselmeier/Novo Nordisk).

Ypsopen Leaflet Standard Cartridge (Opposition EP1827538 Dated May 7, 2010; Haselmeier/Novo Nordisk).

* cited by examiner

INJECTION DEVICE HAVING A ROTATABLE SCALE DRUM

CROSS-REFERENCE TO RELATED APPLICATIONS

This application is a 35 U.S.C. §371 national stage application of International Patent Application PCT/EP2006/050800 (published as WO 2006/084876), filed Feb. 9, 2006, which claims priority of Danish Patent Application Nos. PA 2005 00715, filed May 17, 2005, PA 2005 01252 filed Sep. 8, 2005, and EP Application No. 05002872.9 filed Feb. 11, 2005; this application further claims priority under 35 U.S.C. §119 of U.S. Provisional Application Nos. 60/655,360 filed Feb. 23, 2005, and 60/684,322 filed May 25, 2005.

THE TECHNICAL FIELD OF THE INVENTION

The invention relates to an apparatus such as an injection pen for delivering a drug to the human body preferably in a subcutaneous way.

DESCRIPTION OF RELATED ART

In the disclosure of the present invention reference is mainly made to the treatment of diabetes by injection of insulin; however this is only an exemplary use of the present invention.

Injection pens are mainly made for users who have to inject themselves frequently, e.g. people suffering from diabetes. A number of demands are set to such injection pens. The setting of a dose must be easy an unambiguous and it must be easy to read the set dose. It must be possible with a minimum of trouble to cancel or change a wrongly set dose and when the dose is injected the dose setting must return to zero. When a prefilled injection pen is in question, i.e. an injection pen which is disposed of when the reservoir is empty, the injection pen must further be cheap and made of materials suitable for recycling.

Most dose setting devices work with a threaded piston rod co-operating with a nut where the nut and the piston rod may be rotated relative to each other. The dose setting may be obtained by screwing the nut away from a stop to which it is return during injection by pressing the piston rod forward until the nut member abuts the stop. By other dose setting devices one of the elements, the nut or the piston rod, is kept inrotatable and the other is allowed to rotate a set angle depending on the set dose, whereby the piston rod is screwed forward a distance through the nut member.

In most injection devices for apportioning set doses it is preferred that the piston rod is constantly engaging the piston upon which it works during the injection thereby preventing back suction. To obtain this, precaution is taken to prevent the piston rod from moving backwards in a proximal direction.

A prior art delivery apparatus is disclosed in U.S. Pat. No. 6,004,297. This apparatus disclosed comprises a mechanism for rotating the threaded piston rod such that the thread on the piston rod is screwed forward in a nut connected to the cartridge holder. A one-way ratchet is interfaced between the piston rod and the cartridge holder such that the piston rod can only rotate in one direction relatively to the cartridge holder. The ratchet has an initial reluctance that must be overcome in order for the mechanism to rotate. This reluctance is set large enough to resist the torque exerted when rotating the dose setting knob meaning that only an adequate injection pressure exerted on the dose setting knob will overcome the reluctance and make the driver rotate. In the embodiment disclosed in FIG. 6 to 10, a scale drum is mounted inside the apparatus. The scale drum is axially connected to the dose setting member but is free to rotate relatively to the dose setting member and is forcedly rotated by an interior thread in the housing when axially moved. The set dose can be viewed through a window in the housing.

The tolerances in the thread connection between the scale drum and the housing is decisive for the precision of the display. If the scale drum were e.g. a little loose in the thread an erroneous dose size could be displayed, however if it were too tight in the thread connection, it would be difficult to press back the dose setting knob.

Another injection pen is disclosed in U.S. Pat. No. 6,221,053. In this injection pen the injection button is integral with the scale drum and is rotated up or down a thread provided on the exterior of a driver to set a dose. In order to inject the set dose, the combined injection button and scale drum is pushed back in an axial non-rotatable movement which forces the driver to rotate. Since the driver has an internal thread mating the thread on the keyed piston rod, the keyed piston rod is moved forward through the key available in the nut member inside the housing. Since the scale drum is not rotated during injection a window stretching all 360 degrees of the pen is provided. A second window provided in the driver indicates the set dose.

In this solution, the scale indications are visible over all the 360 degrees that the window stretches. The user most therefore be particular observant to read the set dose through the extra window provided in the driver.

The piston rod drive disclosed in U.S. Pat. No. 6,004,297 and in U.S. Pat. No. 6,221,053 basically comprises two elements. A first element which mates the keyed piston rod and a second element with an inner thread mating the outer thread of the piston rod. The piston rod is moved forward when the first element and the second element are relatively rotated.

In U.S. Pat. No. 6,004,297, the first element is the piston rod guide mating the keyed piston rod and the second element is the threaded nut member which makes the piston rod rotate forward during injection. Whereas in U.S. Pat. No. 6,221,053, the first element is the keyed nut member inrotatable connected to the housing and the second element is the threaded driver. In the latter case, the piston rod is brought forward without rotating.

A different injection pen is disclosed in WO 04/078239. This injection pen comprises a threaded piston rod which is screwed forward in an internal threaded nut when rotated. A drive sleeve having a thread mating the thread of the piston rod rotates the piston rod when moved axially forward. The drive sleeve is coupled to a dose dial sleeve which is rotated to dial up a dose. The dose dial sleeve is rotated out from the housing in order to set up a dose and it is rotated back when the set dose is released. The drive sleeve is rotated together with the dose dial sleeve when a dose is set but prevented form rotation when the set dose is injected.

In use, the dose dial sleeve is rotated out of the housing when a dose is set and it is rotated in the opposite direction when the dose dial sleeve is pressed back to inject the set dose. Thereby the markings on the dose dial sleeve indicating the dose size becomes visible to the user as the dose dial sleeve is screwed out of the housing. Should a user accidentally disturb the rotation of the dose dial sleeve when injecting a dose e.g. by applying a sideway pressure to the dose dial sleeve this would add to the force needed to press back the dose dial sleeve.

From US 2002/0052578 is yet another injection pen known. This injection pen comprises a dose dial sleeve and a drive sleeve. In order to set a dose, the dose dial sleeve is rotated and screwed out from the housing by an internal thread formed in the housing. The dose dial sleeve is coupled to the drive sleeve such that the drive sleeve follows the rotational movement of the dose dial sleeve away from the housing. When a dose is injected, the drive sleeve together with the dose dial sleeve is pressed back towards the housing. This axial movement locks the drive sleeve to the housing such that the drive sleeve can only be moved in an axial direction. At the same time the dose dial sleeve is released from the drive sleeve such that it can rotate back to its zero position. A gear mechanism is provided between the drive sleeve and the piston rod.

A spring is provided between the dose dial sleeve and a radial movable element that secures the axial movement of the drive sleeve during injection. Springs interfaced between rotatable and non-rotatable elements tends to increase the friction of the relative movement between the parts.

Some drugs, such as insulin are self-administered, and the typical diabetes person will require subcutaneous injections of insulin several times during the course of the day. Since most injections of these drugs are performed in private surroundings by the user himself there is a great desire for very simple yet also very precise injection devices.

DESCRIPTION OF THE INVENTION

Having regard to the above-identified prior art devices, it is an object of the present invention to provide a drug delivery device which eliminates disadvantages in the prior art drug delivery devices.

During setting of the dose the scale drum is engaged by the dose setting member such that the scale drum and the dose setting member rotates together. At the same time, the scale drum is decoupled the piston rod drive such that the scale drum can be rotated with out influencing the piston rod drive.

When a dose is injected, and axial pressure is applied to the dose setting member it disengages from the scale drum which rotates back to its initial position as the dose setting member is pushed axially back. At the same time, the scale drum couples to the piston rod drive such that rotation of the scale drum is transmitted to the piston rod drive.

The scale drum is henceforth either coupled to the dose setting member (when setting a dose) or to the piston rod drive (when expelling the set dose).

In this way the scale drum is utilized as a part of the driving mechanism when injecting rather than the scale drum being a slave following the movement of the driver.

In order to couple the scale drum and the piston rod drive together a connector pipe is used. This connector pipe is preferably positioned between the scale drum and the piston rod drive.

The connector pipe is in toothed engagement with the scale drum such that it is connected when an axial pressure is applied to the connector pipe and disconnected preferably by a resilient member when no pressure is applied.

Further, the connector pipe has an interior shape which connects to a rathet guide which is a part of the piston rod drive.

The dose setting member by which the user selects the size of the dose to be injected can be shifted between two different positions in the axial direction.

In the first position the dose setting member is rotational connected to the scale drum such that the dose setting member and the scale drum rotates together.

In the second position, the dose setting member is axially locked such that it can only move in an axial direction. In this position the dose setting member urges the scale drum and the connector pipe together such that rotation of the scale drum is transformed to the connector pipe and henceforth to the ratchet guide.

In order to keep the connector pipe disengages from the scale drum when a dose is being set a resilient element is positioned such that the scale drum and the connector is only connected when the resiliency of that element is overcome.

A shield or housing connector is telescopically connected to the housing. This shield is axially guided in the housing such that it can telescope out of the housing. The dose setting member is releasable connected to this shield such that the dose setting member can rotate relatively to the shield in the first position but is locked to the shield in the second position. This secures the axial movement of the dose setting member when a dose is injected.

Alternatively the shield and the dose setting member can be formed integrally thus forming one rigid element. The combined shield and dose setting member, hereafter referred to as the dose dial is provided with releasable means that can disengage the housing such that the dose dial can rotate relatively to the housing when a dose is set and engage the housing to prevent the dose dial from rotating relatively to the housing when the dose is expelled. These releasable engaging means are preferably formed as a number of flexible protrusions respectively riding over and engaging longitudinal tracks inside the housing.

Since the shield or the dose dial is provided on the outside of the scale drum they are preferably transparent such that the indications on the scale drum are viewable.

The injection device could be provided with a build-in End-of-Dose indicator which provides the user with a tactile and/or sound indication when the set dose is fully injected. The End-of-Dose indicator preferably comprises a cut-away part on the thread guiding the scale drum. The part that is cut away is located at the distal end of the thread such that the thread has an end surface that is generally parallel to the longitudinal direction of the injection device. When a user injects the set dose, the scale drum is rotated down the thread, once the scale drum reaches the end surface, the scale drum will accelerate axially downward thereby providing the user with a tactile and/or audible information that the dosing stroke has reached its end.

DEFINITIONS

An "injection pen" is typically a mechanical i.e. user energized injection apparatus having an oblong or elongated shape somewhat like a pen for writing. Although such pens usually have a tubular cross-section, they could easily have a different cross-section such as triangular, rectangular or square.

As used herein, the term "connected" shall preferably mean that two elements or components are physically joined together, whereas the term "coupled" indicates that another element can be present in between the elements so coupled together i.e. no physical contact between elements coupled together are required. Usually elements that are connected or coupled together can be disconnected or decoupled.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

Correspondingly, the term "subcutaneous" injection is meant to encompass any method of transcutaneous delivery to a subject.

Further the term "injection needle" defines a piercing member adapted to penetrate the skin of a subject for the purpose of delivering or removing a liquid.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be construed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as their relative dimensions are intended to serve illustrative purposes only.

In that context it may be convenient to define that the term "distal end" in the appended figures is meant to refer to the end of the injection device carrying the injection needle whereas the term "proximal end" is meant to refer to the opposite end pointing away from the injection needle.

Figure 1:
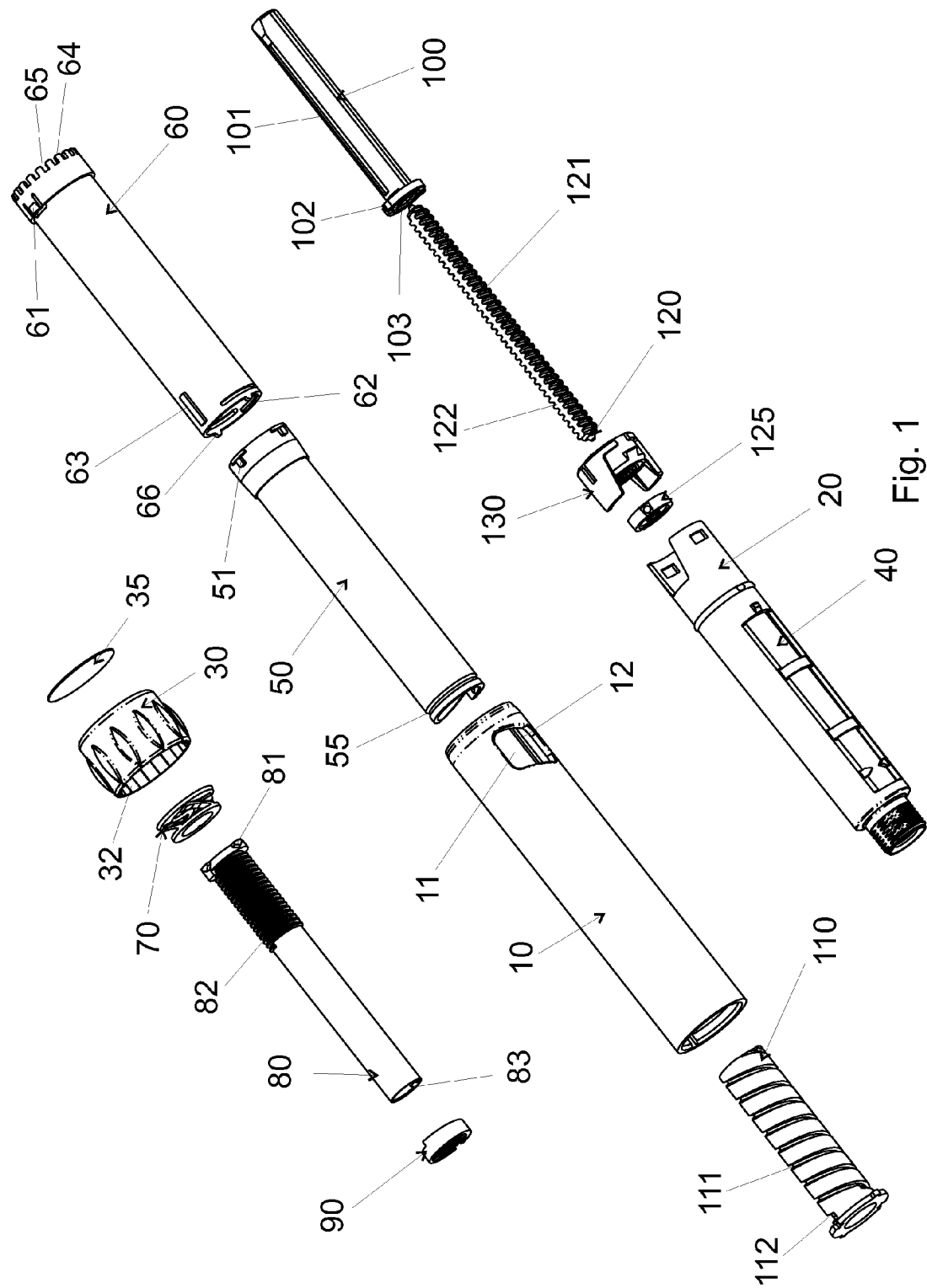
FIG. 1 shows an exploded, perspective view of the injection device.
Figure 2:
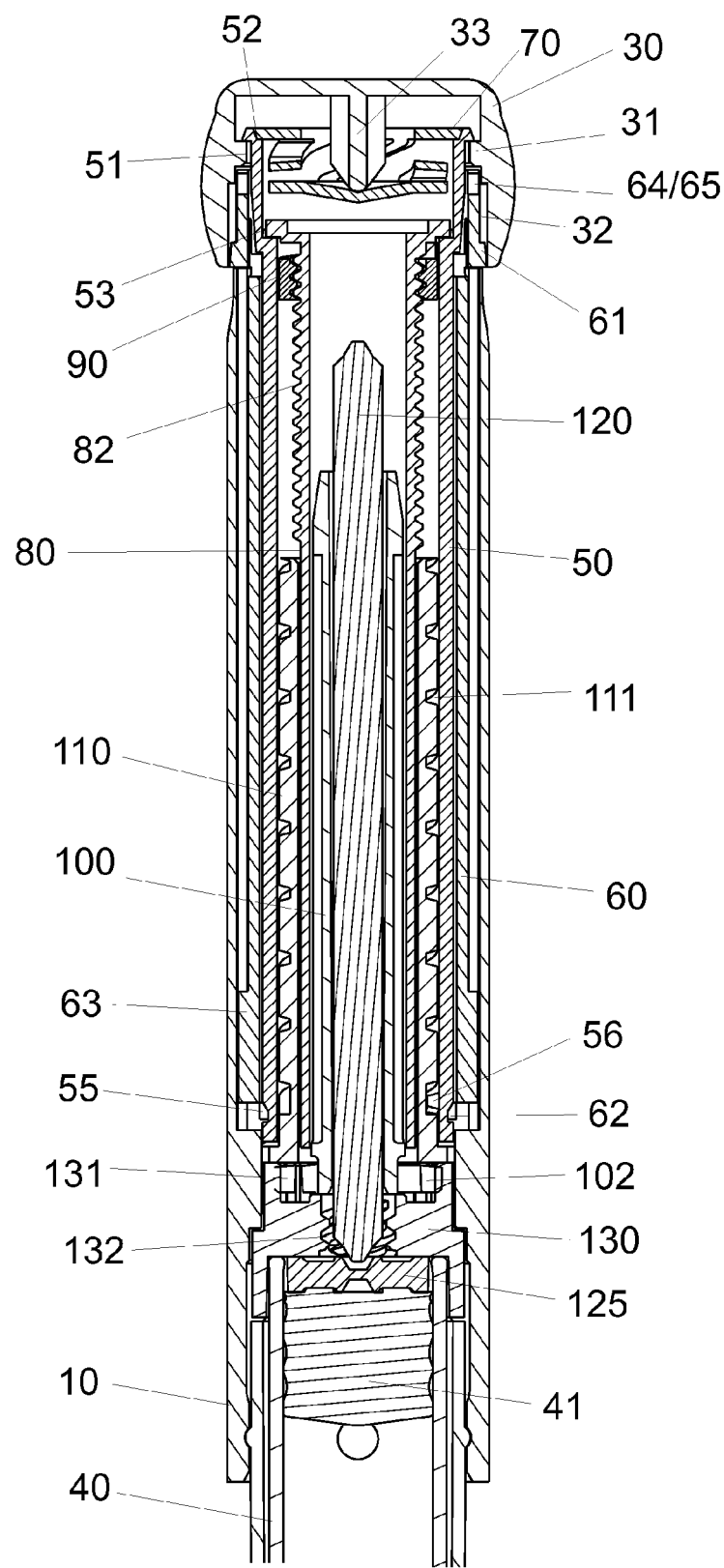
FIG. 2 shows a sectional view of the injection device with no dose set.

FIG. 1 discloses an exploded view of a user energized injection pen comprising a housing 10 and a cartridge holder 20. The housing 10 is provided with a window 11 through which the dose set by rotating the dose setting button 30 and indicated on a scale drum 50 can be viewed. The cartridge holder 20 supports a reservoir 40 containing the drug to be expelled.

The interior of the injection pen is detailed disclosed in the FIGS. 2 to 5.

Figure 3:
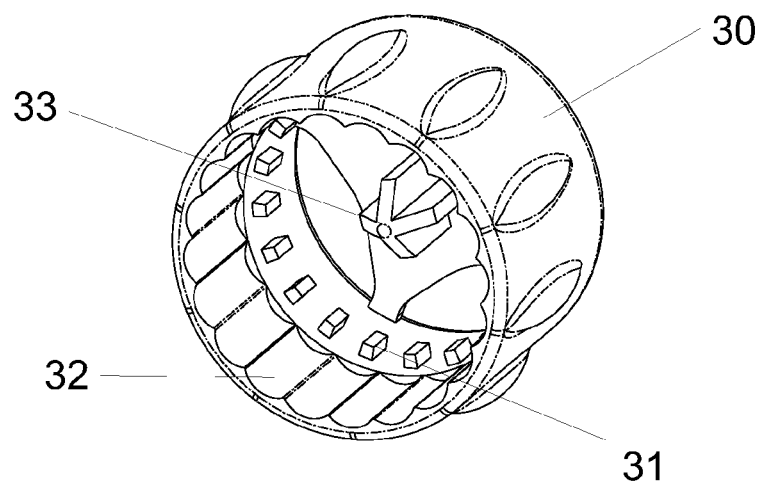
FIG. 3 shows a perspective view of the push button.
Figure 5:
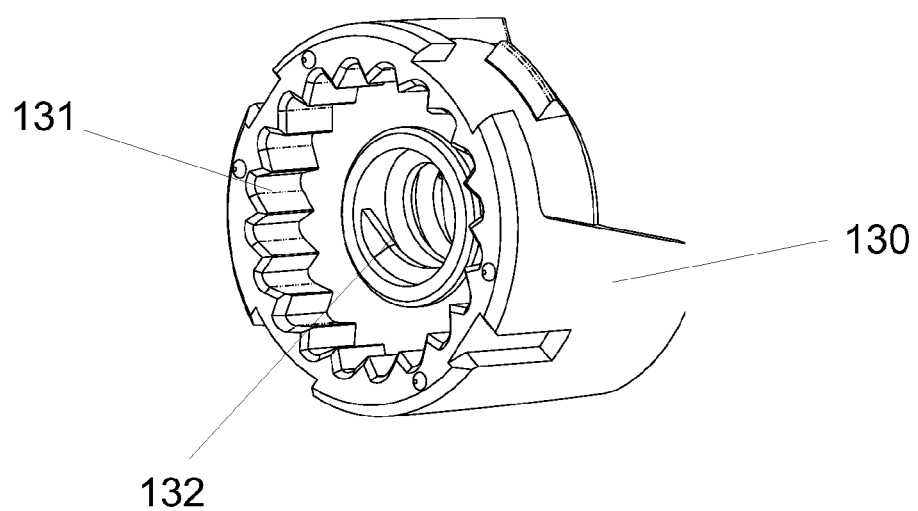
FIG. 5 shows a perspective view of the nut member.

The push button 30 disclosed in details in FIG. 3 is provided at the proximal end of the injection device and connected to the scale drum 50 by a plurality of push button protrusions 31 engaging a number of teeth 51 on the outside periphery of the scale drum 50. A spring 70 pressing on a spear shaped protrusion 33 inside the push button 30 urges the push button 30 and the scale drum 50 in different directions thereby maximising the engagement between the push button protrusions 31 and the external teeth 51. Further a toothed click ring 32 inside the push button 30 rides over one or more click arms 61 provided on the outside surface of the housing connector 60.

The push button 30 could further be provided with a colour indication e.g. for indicating the type of insulin in the injection device. Such colour indication can as in the disclosed example be made as an insert 35 in the push button 30.

Figure 4:
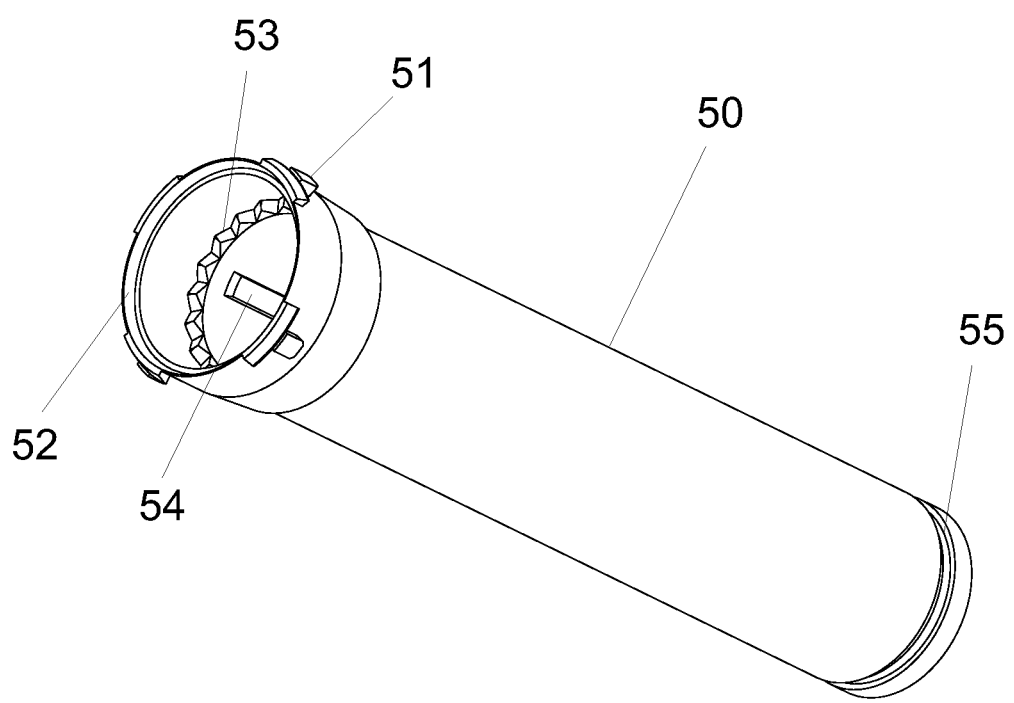
FIG. 4 shows a perspective view of the scale drum.

The scale drum 50 as shown in FIG. 4 is further provided with a recess 52 at the proximal end carrying the spring element 70. Further an internal toothed ring 53 supporting the connector pipe 80 is found on the inside surface of the scale drum 50. A longitudinal track or protrusion 54 interacts with the end-of-content nut 90 as explained later, and a ring shaped track 55 provided at the distal end is engaged by an inwardly pointing protrusion 62 in the housing connector or shield 60.

The housing connector 60 has a protrusion 63 which is guided in a longitudinal track 12 provided on the inside surface of housing 10. In this way the housing connector 60 is rotational locked to the housing 10. Further at the proximal end, the housing connector 60 is equipped with a plurality of teeth 64 separated by longitudinal slits 65, which slits 65 are engaged by the push button protrusions 31 when a dose is expelled.

The connector pipe 80 is at the proximal end provided with a plurality of v-shaped teeth 81 positioned such that the tip of the V-shape engages the toothed ring 53. Further the connector pipe 80 is on its outside provided with a helical End-of-Content track 82 engaged by an end-of-content nut 90 which is axially guided inside the scale drum 50 by the longitudinal track/protrusion 54. The connection pipe 80 is placed inside a thread tower 110 which is inrotatable connected to the housing 10, or alternatively moulded integral with the housing 10.

The thread tower 110 further has an external thread 111 engaging an internal thread 56 provided on the inside surface of the scale drum 50 such that the scale drum 50 can be screwed up and down the thread tower 100.

A ratchet sleeve 100 is located inside the connector pipe 80 and connected through a longitudinal track 101 being engaged by a protrusion 83 on the inside surface of the connector sleeve 80. In this way the connector sleeve 80 and the ratchet sleeve 100 rotates together but can slide axially in relation to each other. At the distal end, the ratchet sleeve 100 terminates in a number of outwardly pointing resilient arms 102, which arms 102 engages a rim of teeth 131 on the inside surface of the nut member 130. The engagement between the resilient arms 102 and the rim of teeth 131 are preferably made such that the ratchet sleeve 100 can only rotate in one direction relatively to the housing 10. On the inside the ratchet sleeve 100 is formed with a non-circular through-going opening 103 engaging the piston rod 120. Further the inside thread 132 of the nut member 130 mates the outside thread 121 of the piston rod 120.

The nut member 130 is engaged with the cartridge holder 20 and embedded in the housing 10 and cartridge holder 20 connection such that the housing 10, the cartridge holder 20 and the nut member 130 forms one unit.

Centrally located in the injection device is the piston rod 120 which, through a piston rod foot 125, activates the reservoir to expel the drug contained therein. In the disclosed example, the reservoir is a cartridge 40 formed from glass or plastic in which a movable piston 41 of e.g. rubber is located. By pressing the piston 41 forward, drug can be expelled through a hollow conduit such as an injection needle preferably for subcutaneous injection mounted to the distal end of the injection device.

The piston rod 120 has an external thread 121 and a keyed surface 122 such that the piston rod 120 rotates with the ratchet sleeve 100. During rotation of the piston rod 120 it is screwed forward in the inside thread 132 of the nut element 130.

In order to set a dose, the user rotates the push button 30 which engages the scale drum 50 through the connection between the push button protrusions 31 and the teeth 51. The scale drum 50 is henceforth screwed up the thread 111 of the thread tower 100.

During the outward rotation of the scale drum 50, the connector pipe 80 follows the scale drum 50. However since the connector pipe 80 is keyed to ratchet sleeve 100 which is prevented from rotation when a dose is set due to the engagement of the arm 102 and the toothed ring 131, the connector pipe 80 is only moved axially with the scale drum 50 while the teeth 81 rides over the toothed ring 53.

The housing connector 60 also follows the movement of the scale drum 50. The movement of the housing connector 60 is however only axial due to engagement between the protrusion 63 and the longitudinal track 12 in the housing 10. The housing connector 60 is lifted away from the housing 10 due to the engagement between the ring shaped track 55 and the inwardly pointing protrusion 62.

As the scale drum 50 is rotated printing on the outside surface of the scale drum 50 indicating the size of the set dose becomes visible in the window 11. The user of the injection device can rotate the scale drum 50 in either direction.

In order for the user to be able to view the indications on the scale drum 50, the housing connector 60 must be at least partial transparent since the housing connector 60 slides on the outside surface of the scale drum 50.

In order to inject the set dose, the user applies an axial force onto the proximal end of the push button 30 which moves the push button protrusions 31 out of the engagement 31 with the external toothed ring 51 and into the engagement with the opened slits 65. The external toothed ring 51 can e.g. be made as a discontinued ring as disclosed in FIG. 4. At the same time, the spear shaped element 33 inside the push button 30 is pressed against the spring 70 and against the connector pipe 80. Due to the engagement between the v-shaped teeth 81 and the internal toothed ring 53, the connection pipe 80 is now locked to scale drum 50.

The push button 30 moves axially as the user applies pressure to the push button 30 due to the engagement between the longitudinal groove 12 inside the housing 10 and the longitudinal protrusion 63 on the housing connector 60. The scale drum 50 locked to the connector pipe 80 rotates as it is screwed down the thread 111 on the thread tower 110.

This rotation of the connector pipe 80 is transformed to a rotation of the ratchet sleeve 100 due to the keyed engagement between the longitudinal protrusion 83 and the longitudinal track 101 of the ratchet sleeve 100 and henceforth to a rotation of the piston rod 120 due to the keyed engagement between the opening 103 and the keyed surface 122 of the piston rod 120.

When the piston rod 120 is rotated it is screwed forward in the thread 132 of the nut member 130. This forward movement of the piston rod 120 is transmitted to the drug contained in the reservoir 40 through the piston foot 125 and the piston 41, which forces the drug to be expelled through a hollow conduit such as an injection needle mounted to the distal end of the injection device.

An additional embodiment is disclosed in the FIGS. 6 to 9. In this embodiment the previous elements the push button 30 and housing connector 60 is shaped as one element hereafter called the dial 150.

The dial 150 is at its distal end provided with a number of protrusions 151. These protrusions 151 are resilient e.g. due to cut-outs 152 in the material making up the dial 150.

The scale drum 50 is at its distal end provided with a ring shaped track 57 having a sloping bottom which tapers toward the distal end of the scale drum 50.

Figure 6:
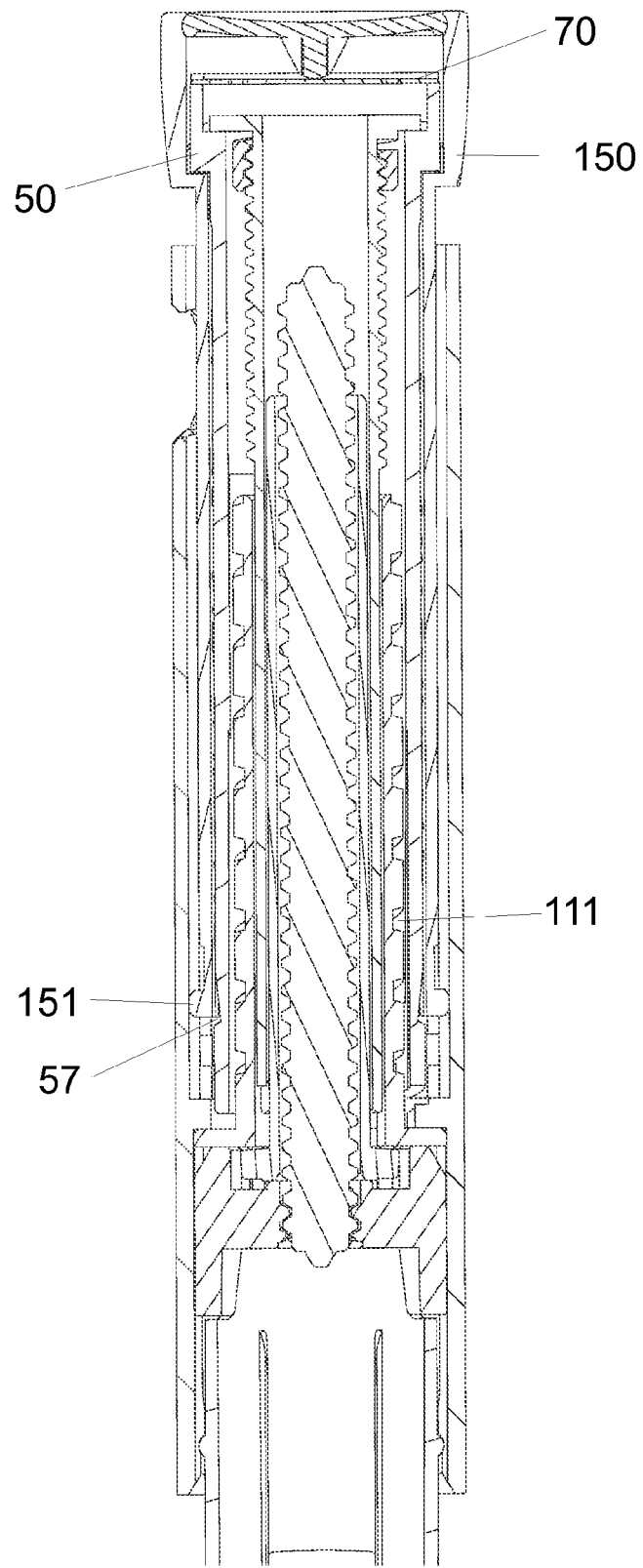
FIG. 6 shows a sectional view of an embodiment with a dose set.

When setting a dose as depictured in FIG. 6, the resilient protrusion 151 is located right above the ring shaped track 57 which allows the resilient protrusion 151 to bounce and click over longitudinal grooves 15 (FIG. 8) on the inside surface of the housing 10 when rotated.

Since the dial 150 is rotational coupled to the scale drum 50 due to the pressure of the spring element 70 and the engagement between teeth 153 on the dial 150 and teeth 51 on the scale drum 50, the dial 150 and the scale drum 50 is screwed out of the housing 10 together when the dial 150 is rotated.

Figure 7:
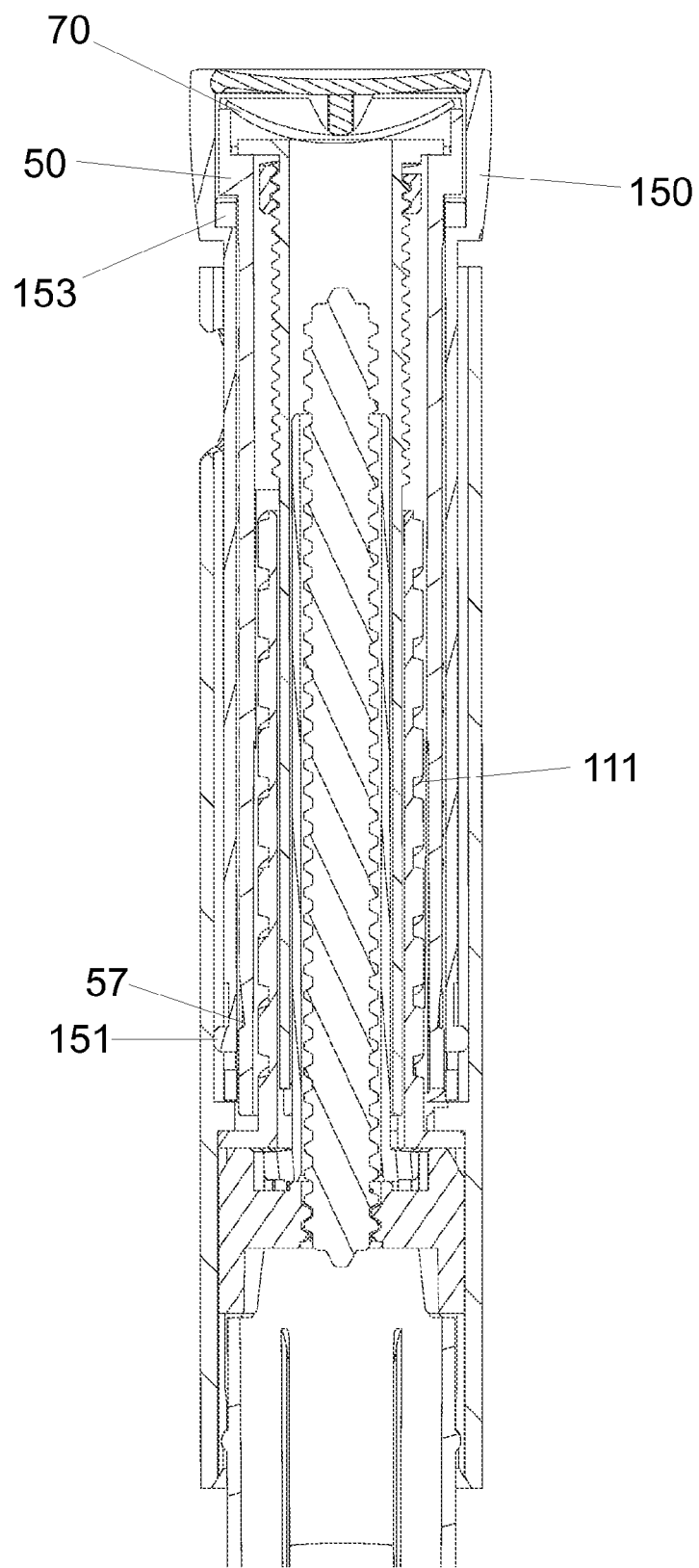
FIG. 7 shows a sectional view of the embodiment of FIG. 6 during injection.

When the set dose is to be injected as disclosed in FIG. 7 the user pushes back the dial 150. Since the scale drum 50 is engaged by the thread 111, this axial movement releases the dial 150 from the scale drum 50 by moving the dial 150 axially relatively to scale drum 50.

The axial movement of the dial 150 brings the protrusions 151 into a position where they are no longer located above the ring shaped track 57. This inhibits the resiliency of the protrusion 151 which is hereafter axially guided in the longitudinal grooves 15 in the housing 10.

The injection pen disclosed in the FIGS. 1 to 7 all has the threaded piston rod 120 engage an internal thread 132 in the nut member 130 such that the piston rod is screwed forward when rotated.

Figure 8:
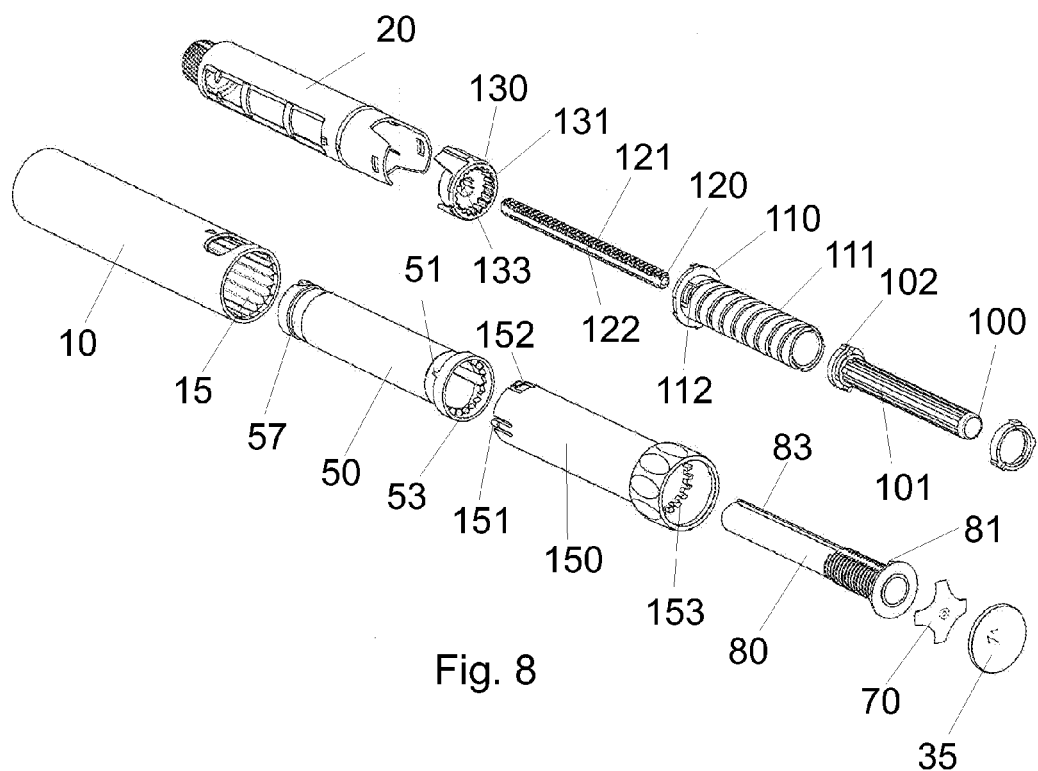
FIG. 8 shows an exploded view of an embodiment.
Figure 9:
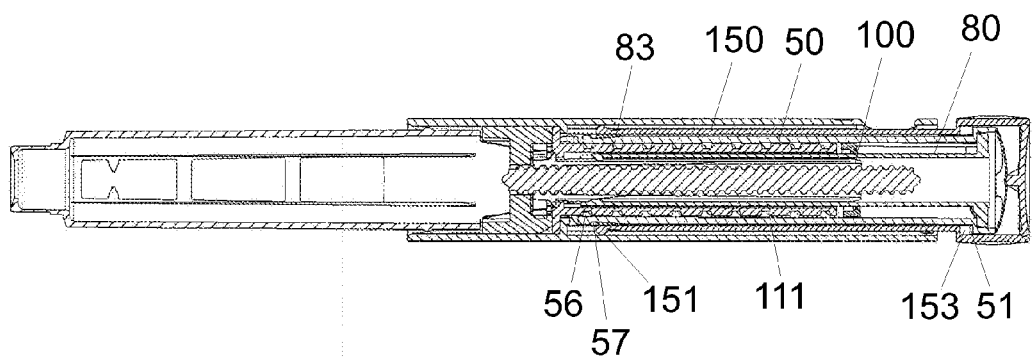
FIG. 9 shows a sectional view of the embodiment in FIG. 8.

FIGS. 8 and 9 discloses an alternative where the nut member 130 is provided with an internal key 133 mating the keyed surface 122 of the piston rod 120. At the same time, the outside thread 121 of the piston rod 120 mates an internal thread 104 on the inside surface of the ratchet sleeve 100 such that when the ratchet sleeve 100 and the nut member 130 is rotated relatively, the piston rod 120 is brought forward without rotating.

When a user dials a dose by rotating the dial 150 this rotation is transformed to the scale drum 50 by the engagement between the teeth 51 and the toothed rim 153. Since the connector pipe 80 is locked to the ratchet 100 through protrusion 83 and track 101, the connector pipe 80 is prevented from rotation. The scale drum 50 and the dial 150 screws proximally out of the housing 10 due to helical track 111 while the protrusions 151 clicks over the longitudinal grooves 15 inside the housing 10. In order to view the non-showed settings printed on the scale drum 50 the dial 150 must be at least partly transparent.

When injecting, the user presses back the dial 150 which moves axially relatively to the scale drum 50 such that the protrusions 151 are moved to a position where they are supported by the scale drum 50 on their backside making the protrusion 151 more rigid. Due to the engagement between the protrusions 151 and the longitudinal tracks 15 in the housing 10, the dial 150 is returned axially, however it can rotate if the protrusions 151 changes tracks 15 without disturbing the function of the injection device.

The pressure applied to the dial 150 also presses the teeth 81 of the connector pipe 80 into engagement with the toothed ring 53 of the scale drum 50 such that the connector pipe 80 rotates together with the scale drum 150 as it rotates down the thread 111. This rotation drives the ratchet 100 to rotate which moves the piston rod 120 forward in the key 133. In this way the connector pipe 80 operates as the driving element and rotates relatively to the housing 10.

The nut member 130 could in all embodiments be designed as a separate insert which is rotatable relatively to housing 10 such that the piston rod 120 can be brought forward by rotating the nut member 130. The rotatability of the nut member 130 can be predetermined to a specific number of degrees such that relative rotation of the nut member 130 and the housing 10 causes a predetermined small amount of insulin to be delivered. In this way a so called air shot can be performed by rotating the nut member 130 and the housing 10 relatively. The nut member 130 is preferably rigidly connected to the cartridge holder 20 such that relative rotation of the cartridge holder 20 and the housing 10 causes the piston rod 120 to move forward a predetermined distance. The interface between the rim of teeth 131 in the nut member 130 and the resilient arms 102 on the ratchet sleeve 100 secures that the piston rod 120 can only be moved in one direction. Such air shot mechanism is described in details in pending patent application No. PCT/DK2004/000818.

The injection pen disclosed also has a build-in End-of-Dose indicator which provides the user with both a tactile and sound indication when the set dose is fully injected. The End-of-Dose indicator comprises a cut-away part on the thread tower 110. The part that is cut away is located at the distal end of the thread 111 such that the thread 111 has an end surface 112 that is generally parallel to the piston rod 120. The end surface 112 is preferably 2-5 mm long.

When a user injects the set dose, the scale drum 50 is rotated down the thread 111 on the thread tower 110. Once the internal thread 56 in the scale drum 50 reaches the end surface 112, the scale drum 50 will continue axially downward thereby providing the user with a tactile information that the dosing stroke has reached its end. This drop along the end surface 112 will also provide a distinct sound as the scale drum 50 is accelerated into the button of the thread tower 110 or the housing 10. The geometry of the internal thread 56 of the scale drum 50 and the length of the cut away end surface 112 is decisive for the intensity of the tactile and/or sound indication.

In order to reset the sound producing means to be able to generate the tactile and/or sound again a new dose must be set such that the internal thread 56 is moved a distance up the internal thread 111. To do so the internal thread 56 must be lifted up to alignment with the start of the thread 111 this can e.g. be done by providing the distal end of the scale drum 50 with a resilient member 66 (FIG. 1) or by providing a steep slope on the end surface 112.

The resilient member 66 will lift the scale drum 50 and thereby the internal thread 56 in the scale drum 50 in relation the thread tower 110 such that the internal thread 56 aligns the thread 111 on the internal thread tower 110 above the end surface 112. When the user sets a new dose to be injected, the internal thread 56 will be dialed up the thread 111 and be ready to deliver a new end of dose indication.

A steep slope on the end surface 112 will make the internal thread 56 crawl up this steep slope and into the thread 111 when the user sets a new dose to be injected. When the user keeps dialing the thread 56 will be dialed up the thread 111 and be ready to deliver a new end of dose indication.

Figure 10:
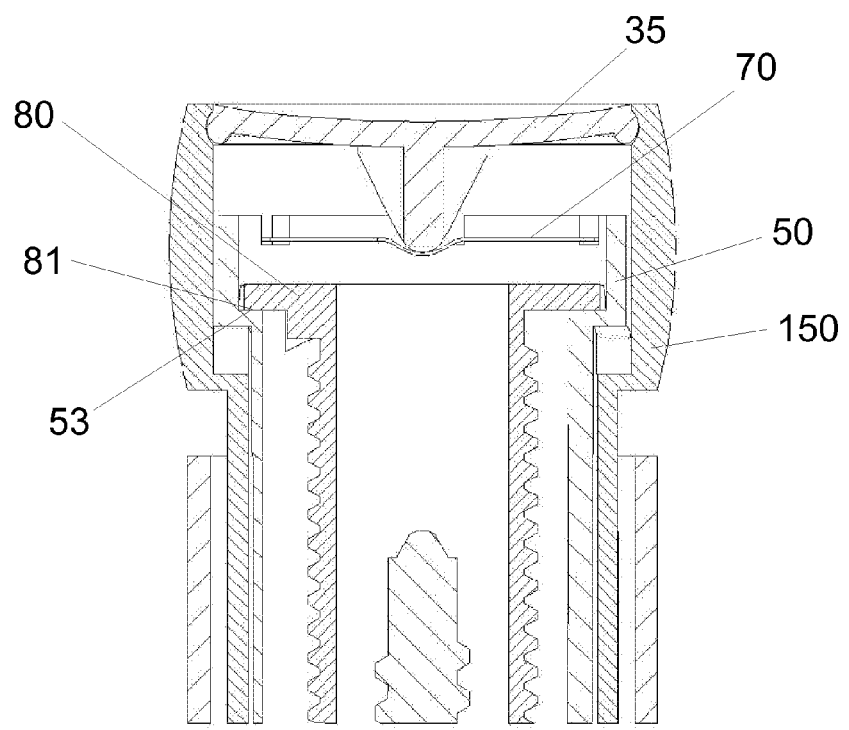
FIG. 10 shows an enlarged view of the top of the embodiment in FIGS. 1 to 5.

FIG. 10 discloses an enlarged view of the connection between the dial 150, the scale drum 50 and the connector pipe 80. Once the user pushes the dial 150 to inject a dose, the insert 35 pushes down the spring 70 to abut the connector pipe 80 whereby the v-shaped teeth 81 positioned on the connector pipe 80 is brought into engagement with the internal toothed ring 53 on the scale drum 50 such that the connector pipe 80 rotates together with the scale drum 50. The teeth making up the toothed ring 53 also has a v-shaped form.

Figure 12:
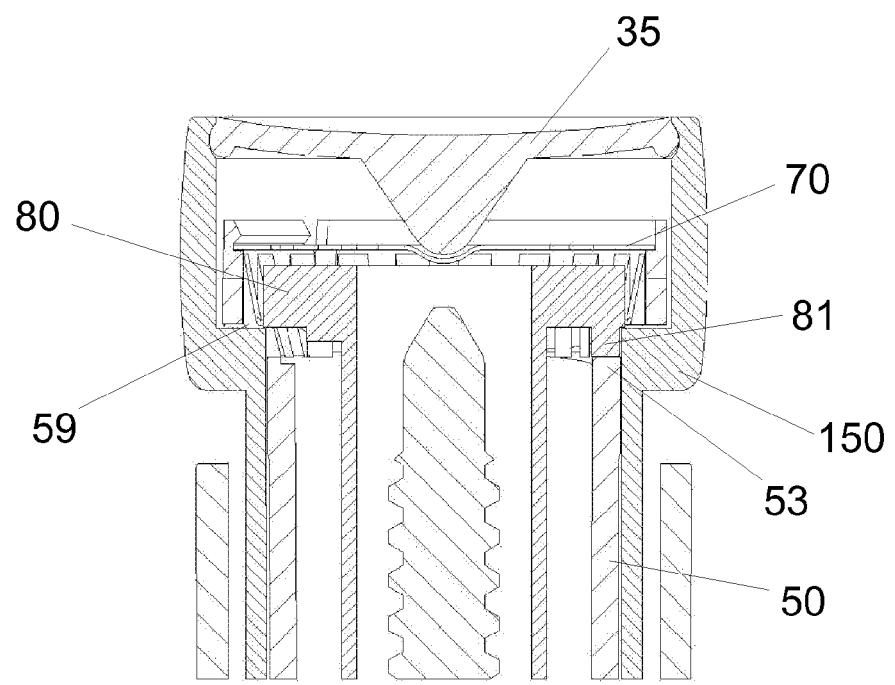
FIG. 12 shows an enlarged view of a different alternative.

In stead of using v-shaped teeth for the engagement between the scale drum 50 and the connector pipe 80, teeth with parallel surfaces can be used as disclosed in FIG. 12 and FIG. 13.

Figure 11:
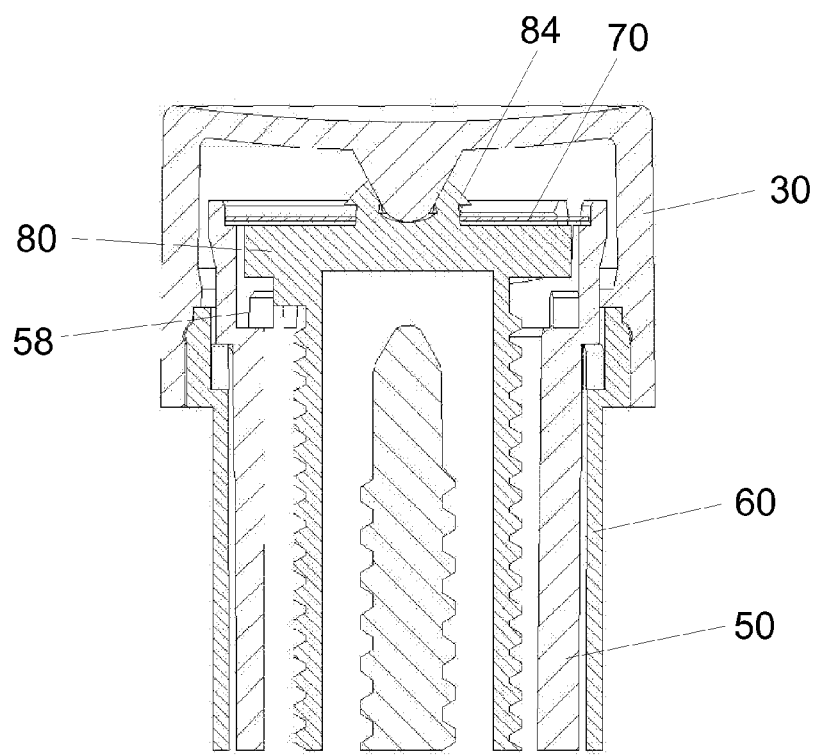
FIG. 11 shows an enlarged view of an alternative top.

In FIG. 11 the individual teeth of the toothed ring 53 has parallel surfaces 58 as has the teeth 81 on the connector pipe 80, which means that the teeth 81 on connector pipe 80 can not ride over the teeth of the toothed ring 53 but must be actively lifted out of the engagement. This is done by connecting the spring 70 to the connector pipe 80 by having a hook 84 on the connector pipe 80 engage an opening in the spring 70. When a user no longer pushes on the dose setting button 30, the spring 70 will lift the connector pipe 80 out of engagement with the scale drum 50 such that the scale drum 50 can rotate relatively to the connector pipe 80. When a pressure is applied to the dose setting button 30, the scale drum 50 and the connector pipe 80 engages and rotates together.

All though the dose setting button 30 and the housing connector 60 is illustrated as two individual elements they could also be made as one rigid element (dose dial 150) as disclosed in the FIGS. 6 to 11 and in FIG. 13.

In the embodiment disclosed in FIG. 12, the scale drum 50 is perforated by a plurality of openings 59 such that part of the connector pipe 80 abuts the dose dial 150 through these openings 59. When no pressure is applied on the insert 35, the dial 150 actively lifts the teeth 81 on the connector pipe 80 out of engagement with the toothed ring 53 of the scale drum 50 due to the abutment of the connector pipe 80 with the dose dial 150 through the openings 59. In this disengaged position the connector pipe 80 and the scale drum 50 can rotate relatively. When pressure is applied during injection, and the dial 150 is moved in the distal direction, the pressure on the spring 70 moves the teeth 81 of the connector pipe 80 into engagement with the toothed ring 53 of the scale drum 50 such that the connector pipe 80 and the scale drum 50 rotates together.

Some preferred embodiments have been shown in the foregoing, but it should be stressed that the invention is not limited to these, but may be embodied in other ways within the subject matter defined in the following claims. On obvious choice would be to mate the key of the piston rod with the interior of the nut member and provide a thread inside the ratchet guide mating the thread of the piston rod. Also the nut member could be moulded integrally with the housing or with the cartridge holder in which case the cartridge could be inserted in the cartridge holder form its distal end.

The invention claimed is:

1. An injection device for apportioning set doses of a drug from a reservoir comprising:
a housing,
a piston rod that has a non-circular cross section and an outer thread and rotates during expelling of the drug from the reservoir, and
a piston rod drive comprising:
a first drive element mating the non-circular cross section of the piston rod to allow axial displacement but not rotation of the piston rod in relation to first drive element,
a second drive element which has an inner thread mating the thread of the piston rod, a dose setting and injection mechanism comprising a dose setting member associated with the piston rod drive through a thread connection along which the dose setting member is structured to be screwed away from the proximal end of the housing a distance determined by the angle of rotation and which thread connection by axial returning of the dose setting member transforms this axial movement to a rotation of one of the first or second drive elements relative to the other, wherein a scale drum is releaseably coupled to the dose setting member to follow rotation of the dose setting member when a dose is set and which scale drum is released from the dose setting member and coupled to the piston rod drive when the set dose is expelled.

2. The injection device according to claim 1, whereinthe scale drum is coupled to the piston drive through a connector pipe interfaced between the scale drum and the piston rod drive.

3. The injection device according to claim 2, wherein the connector pipe is interfaced between the scale drum and a ratchet guide.

4. The injection device according to claim 3, wherein the dose setting member is axial displaceable between a first and a second position, wherein the dose setting member;
in its first position is rotational connected to the scale drum, and
in its second position is axially locked in relation to the scale drum.

5. The injection device according to claim 4, wherein a resilient element urges the dose setting member into the first position when no axial force is applied to the dose setting member.

6. The injection device according to claim 4, wherein the dose setting member in its second position is locked to a longitudinal movable shield which is guided in a longitudinal track on the inside periphery of the housing.

7. The injection device according to claim 6, wherein the shield or a dose dial member is at least partly transparent, such that indications on the scale drum is viewable.

8. The injection device according to claim 4, wherein the dose setting member is formed integrally with a movable shield to form one rigid on a dose dial member.

9. The injection device according to claim 2, wherein the connector pipe is rotational connected to the scale drum upon exertion of an axial force on the dose setting member.

10. The injection device according to claim 1, wherein the thread connection is abruptly disconnected at the end of a dose stroke to provide a tactile and/or sound indication.

* * * * *